(12) United States Patent
Lyles et al.

(10) Patent No.: US 7,037,304 B2
(45) Date of Patent: May 2, 2006

(54) IMPLANTABLE SYSTEM FOR CELL GROWTH CONTROL

(75) Inventors: Mark B. Lyles, San Antonio, TX (US);
Charles A. McLaughlin, Tega Cay, SC (US); Glenn A. Halff, San Antonio, TX (US); William A. Mallow, Helotes, TX (US)

(73) Assignee: Materials Evolution and Development USA, Inc., San Antonio, TX (US)

( * ) Notice: Subject to any disclaimer, the term of this patent is extended or adjusted under 35 U.S.C. 154(b) by 122 days.

(21) Appl. No.: 09/961,479

(22) Filed: Sep. 24, 2001

(65) Prior Publication Data

US 2002/0120251 A1   Aug. 29, 2002

Related U.S. Application Data

(63) Continuation of application No. 09/170,574, filed on Oct. 13, 1998, now Pat. No. 6,340,360, which is a continuation of application No. 08/569,107, filed as application No. PCT/US94/07581 on Jul. 1, 1994, now Pat. No. 5,964,745, which is a continuation-in-part of application No. 08/087,615, filed on Jul. 2, 1993, now abandoned.

(30) Foreign Application Priority Data

Jul. 1, 1994   (WO) ............... PCT/US94/07581

(51) Int. Cl.
*A61K 9/22* (2006.01)
(52) U.S. Cl. .................... 604/891.1; 424/422
(58) Field of Classification Search ............. 604/891.1; 424/422, 423, 425; 623/1.1, 11.11, 1.42, 623/1.43, 1.54; 435/180
See application file for complete search history.

(56) References Cited

U.S. PATENT DOCUMENTS 4,044,404 A * 8/1977 Martin et al. ............... 623/1.54

(Continued)

FOREIGN PATENT DOCUMENTS

WO   9110470   7/1991

OTHER PUBLICATIONS

"New Challenges in Biomaterials," Peppas et al., Science, vol. 263, Mar. 25, 1994, pp. 1715-1720.

(Continued)

*Primary Examiner*—Julian W. Woo
(74) *Attorney, Agent, or Firm*—Baker Botts L.L.P.

(57) ABSTRACT

An implantable infection shield and system for drug delivery in vascular tissue includes a relatively non-biodegradable porous linked fibrous biomaterial which controls and directs cell growth and angiogenesis from adjacent vascular tissue into the implant. Infection shield embodiments stimulate cell growth and angiogenesis from adjacent vascular tissue which effectively blocks passage of pathogenic microorganisms along percutaneously implanted objects. In embodiments for drug delivery, a reservoir of the same biomaterial may contain either (1) a cell culture system enclosed within a porous sealable interior chamber or (2) a biodegradable matrix in which one or more drugs are dispersed. After implantation of a reservoir of the first embodiment in an organism, cultured cells obtain food and oxygen via diffusion in tissue fluid through the porous walls of the interior chamber, while metabolic products, including drugs, diffuse away from the cell culture in an analogous manner. In a reservoir of the second embodiment, a biodegradable matrix substantially fills the pores (voids), and progressive dissolution of the matrix releases one or more drugs into surrounding tissue fluid. Reservoirs of either embodiment comprise a plurality of voids of a predetermined size effective for stimulating angiogenesis from the surrounding vascular tissue into at least a portion of the reservoir. The reservoir thus acts to couple a source: of drugs to the circulatory system of the organism.

12 Claims, 4 Drawing Sheets

U.S. PATENT DOCUMENTS

| | | | | |
|---|---|---|---|---|
| 4,104,426 | A | | 8/1978 | Gonzalez et al. ............. 428/36 |
| 4,148,962 | A | | 4/1979 | Frosch et al. ................ 428/366 |
| 5,024,671 | A | * | 6/1991 | Tu et al. ....................... 623/1.1 |
| 5,201,728 | A | | 4/1993 | Giampapa |
| 5,629,186 | A | * | 5/1997 | Yasukawa et al. .......... 435/180 |
| 5,681,572 | A | * | 10/1997 | Seare, Jr. ..................... 424/423 |
| 5,770,417 | A | * | 6/1998 | Vacanti et al. .............. 435/180 |
| 5,964,745 | A | * | 10/1999 | Lyles et al. ............... 604/891.1 |
| 6,031,148 | A | * | 2/2000 | Hayes et al. ............. 623/11.11 |

OTHER PUBLICATIONS

"Tissue Engineering," Langer et al., Science, vol. 260, pp. 920-926, May 14, 1993.

"Tissue Engineering Using Cells and Synthetic Polymers," Mooney et al., Transportation Reviews, vol. 7, No. 3 (Jul.), 1993; pp. 153-162, Jul. 1993.

"Stabilized Polyglycolic acid fibre-based tubes for tissue engineering," Mooney et al., Biomaterials, vol. 17, No. 2, pp. 115-124, 1996.

"Transport characterization of membranes for immunoisolation," Dionne et al., Biomaterials, vol. 17, No. 3, pp. 257-266, 1996.

"Characterization of the formation of interfacially photopolymerized thin hydrogels in contact with arterial tissue," Lyman et al., Biomaterials, vol. 17, No. 3, pp. 359-364, 1996.

"Biointeractive polymers and tissue engineered blood vessels," Greisler et al., Biomaterials, vol. 17, No. 3, pp. 329-336, 1996.

"Kinetics of bone cell organization and mineralization on materials with patterned surface chemistry,", Healy et al., Biomaterials, vol. 17, No. 2, pp. 195-208, 1996.

"Conditions which promote mineralization at the bone-implant interface: a model in vitro study," Dee et al., Biomaterials, vol. 17, No. 2, pp. 209-215, 1996.

"Role of material surfaces in regulating bone and cartilage cell response," Boyan et al., Biomaterials, vol. 17, No. 2, pp. 137-146, 1996.

"Bone-Grafting Materials in Implant Dentistry," Misch et al., Implant Dentistry, vol. 2, No. 3, pp. 158-167, No Date.

"Anorganic Bovine Bone and Ceramic Analogs of Bone Mineral as Implants to Facilitate Bone Regeneration," Myron Spector, PhD, Clinics In Plastic Surgery, vol. 21, No. 3, pp. 437-444, Jul. 1994.

"Bioactive Factors and Biosynthetic Materials in Bone Grafting," Hollinger et al., Clinics in Plastic Surgery, vol. 21, No. 3, pp. 415-418, Jul. 1994.

"Tissue-Engineered Morphogenesis of Cartilage and Bone by Means of Cell Transportation Using Synthetic Biodegradable Polymer Matrices," Vacanti et al., Clinics in Plastic Surgery, vol. 21, No. 3, pp. 445-462, Jul. 1994.

"Biomaterials in orthopaedic surgery: effects of different hydroxyapatites and demineralized bone matrix on proliferation rate and bone matrix synthesis by human osteoblasts," Zambonin et al., Biomaterials, vol. 16, No. 5, pp. 397-402, 1995.

"Bone and Cartilage Reconstruction with Tissue Engineering Approaches," Vacanti et al., Otolaryngologic Clinics of North America, vol. 27, No. 1, pp. 263-276, Feb. 1994.

"Osteogenesis in muscle with composite graft of hydroxyapatite and autogenous calvarial periosteum: a preliminary report,"Kurashina et al., Biomaterials , vol. 16, No. 2, pp. 119-123, 1995.

"Effect of Bioactive Glass Templates on Osteoblast Proliferation and In Vitro Synthesis of Bone-Like Tissue," Ducheyne et al., Journal of Cellular Biochemistry 56:162-167 (1994).

"Biotechnology and Bone Graft Substitutes," Kenley et al., Pharmaceutical Research, vol. 10, No. 10, 1993, pp. 1393-1401, 1993.

"Implantation of sepiolite-collagen complexes in surgically created rat calvaria defects," Herrera et al., Biomaterials 1995, vol. 16, No. 8, pp. 625-631.

"Recombinant human bone morphogenetic protein-2 is superior to demineralized bone matrix in repairing craniotomy defects in rats," Marden et al., Journal of Biomedical Materials Research, vol. 28, 1127-1138 (1994).

"Facial Bone Healing and Bone Grafts," Paul N. Manson, MD, Clinics in Plastic Surgery, vol. 21, No. 3, Jul. 1994, pp. 331-348, Jul. 1994.

"Bone Grafts and Bone Induction Substitutes," Habal et al., Clinics in Plastic Surgery, vol. 21, No. 4, Oct. 1994, pp. 525-542.

"The Effect of Osteogenin (a Bone Morphogenetic Protein) on the Formation of Bone Orthopic Segmental Defects in Rats," Stevenson et al., The Journal of bone and Joint Surgery, vol. 76-A, No. 11, Nov. 1994, pp. 1676-1687.

"Histomorphometric Analysis of the Repair of a Segmental Diaphyseal with Ceramic and Titanium Fibermetal Implants: Effects of Bone Marrow," Wolff et al., Journal of Orthopaedic Research, vol. 12, No. 3, 1994, pp. 439-446, No Date.

"Symbiosis of Biotechnology and Biomaterials: Applications in Tissue Engineering of Bone and Cartilage,"A.H. Reddi, Jounal of Cellular Biochemistry, 56: 192-195 (1994).

"Bioactive material template for in vitro synthesis of bone," El-Ghannam et al., Journal of Biomedical Materials Research, vol. 29, 359-370, 1995.

"Effect of basic fibroblast growth factor on cartilage regeneration in chondrocyte-seeded collagen sponge scaffold," Fujisato et al., Biomaterials 1996, vol. 17, No. 2, pp. 155-162.

"Use of porous polyurethanes for meniscal reconstruction and meniscal protheses," deGroot et al., Biomaterials 1996, vol. 17, No. 2, pp. 163-173.

"Healing of chondral and osteochondral defects in a canine model: the role of cultured chrondocytes in regeneration of articular cartilage," Shortkroff et al., Biomaterials 1996, vol. 17, No. 2, pp. 147-154, 1996.

"Bone Formation by Osteobalst-Like Cells in a Three-Dimensional Cell Culture," Casser-Bette et al., Calcif Tissue Int (1990), 46:46-56.

"Attachment and proliferation of osteoblasts and fibroblasts on biomaterials for orthopaedic use," Hunter et al., Biomaterials 1995, vol. 16, No. 4, pp. 287-295.

"The Culture of Human Osteoblasts upon Bone Graft Substitutes," Begley et al., Bone, 14, 661-666, (1993).

"Development of a Bioartificial Liver Using Isolated Hepatocytes," Vivek Dixit, Artificial Organs, Vol. 18, No. 5, 1994, pp. 371-384.

"Hepatic Tissue Engineering," Yarmush et al., Annals of New York Academy of Sciences, pp. 238-252, No Date.

"Entrapment of Hepatocyte Spheroids in a Hollow Fiber Bioreactor as a Potential Bioartificial Liver," Wu et al., Tissue Engineering, vol. 1, No. 1, 1995, pp. 29-40.

"Culture matrix configuration and composition in the maintenance of hepatocyte polarity and function," Moghe et al., Biomaterials 1996, vol. 17, No. 3, pp. 373-385.

"Toward development of an implantable tissue engineered liver," Davis et al., Biomaterials 1996, vol. 17, No. 3, pp. 365-372.

"Biodegradable sponges for hepatocyte transplantation," Mooney et al., Journal of Biomedical Materials Research, vol. 29, 959-965 (1995).

"Engineering of a sugar-derivatized porous network for hepatocyte culture," Gutsche et al, Biomaterials 1996, vol. 17, No. 3, pp. 387-393.

"Hepatocyte Culture on Biodegradable Polymeric Substrates," Cima et al., Biotechnology and Bioengineering, vol. 38, pp. 145-158 (1991).

"Evolution of the Bioartificial Liver: The Need for Randomized Clinical Trials," Nyberg et al., The American Journal of Surgery, vol. 166, Nov. 1993, pp. 512-521.

"Delivery of Whole Liver-Equivalent Hepatocyte Mass Using Polymer Devices and Hepatotrophic Stimulation," Uyama et al., Transplantation, vol. 55, 932-935, No. 4, Apr. 1993.

"Hepatocyte Transplantation: Development of New Systems for Liver Repopulation and Gene Therapy," Gupta et al., Seminars in Liver Disease—vol. 12, No. 3, 1992, pp. 321-331.

"Extracorporeal Application of a Gel-Entrapment, Bioartificial Liver: Demonstration of Drug Metabolism and Other Biochemical Functions," Nyberg et al., Cell Transplantation, vol. 2, No. 6, 1993, pp. 441-452.

"Use of Hepatocyte Cultures for Liver Support Bioreactors," Jorg C. Gerlach, Hepatic Encephalopathy, Hyperammonemia, and Ammonia Toxicity, pp. 165-171.

"Hepatocyte culture systems for artificial liver support: Implications for critical care medicine (bioartificial liver support)," Nyberg et al., Critical Care Medicine, vol. 20, No. 8, Aug. 1992, pp. 1157-1168.

"Treating Diabetes with Transplanted Cells," Paul E. Lacy, Scientific American Jul. 1995, pp. 50-58.

* cited by examiner

IMPLANTABLE SYSTEM FOR CELL GROWTH CONTROL

The present application is a continuation of U.S. application Ser. No. 09/170,574, filed Oct. 13, 1998, now U.S. Pat. No. 6,340,360; which is a continuation of U.S. application Ser. No. 08/569,107, filed Mar. 18, 1996, which is a 371 of PCT/US94/07581, now U.S. Pat. No. 5,964,745; which is a continuation-in-part of U.S. application Ser. No. 08/087,615, filed Jul. 2, 1993, now abandoned.

BACKGROUND

Field of the Invention

The invention relates to methods and apparatus for control of cell growth, including angiogenesis, in porous implants, produced from ceramics, of the low density type from the general family described in Banas, et al, *Thermophysical and Mechanical Properties of the HTP Family of Rigid Ceramic Insulation Materials*, AIAA 20the Termophysics Conference, Jun. 19–21, 1985, Williamsburg, Va. (incorporated herein by reference), Creedon, et al., *Strength and Composites*, SAMPLE Quarterly, October and (incorporated herein by reference), U.S. Pat. No. 4,148,962, issued to Leiser, et al. on April 1979 (incorporated herein by reference). As an example of the general family, a thermal insulation material is produced by Lockheed Misseles & Space Company, Inc. of Sunnyvale, Calif., having the following properties, according to what is believed to be an Occupational Health and Safety Administration Material Data Sheet of Feb. 28, 1989, as follows:

I. Product Identification

Trade name (as labeled): HTP (High Thermal Performance) Material Chemical names, common names: Thermal insulation material.
Manufacturer's name: Lockheed Missiles & Space Company, Inc.
Address: 1111 Lockheed Way, Sunnyvale, Calif. 94089

| Emergency phone: | (408) 742-7215 (6 a.m.–5 p.m. PST) | Refer questions to: Lockheed Missiles & Space Company, Inc. |
|---|---|---|
| | (408) 742-3536 | Occupational Safety & Health Dept. |
| | (Off Hours) | Org/4720-8/106 |
| Business phone: | (408) 742-7215 | Date prepared: 1/89 |

II. Ingredients

| | | | Exposure Limits in Air | | |
|---|---|---|---|---|---|
| Chemical Names | Gas Numbers | Percent (by vt.) | OSHA (PEL) | AGGIH (TLV) | Other |
| Alumina Fiber | 1344-28-1 | 10–50 | 5 mg/m$^3$/ 15 mg/m$^3$ (Respirable/ Total dust) | 10 mg/m$^3$ (Total nuisance dust) | |
| Silica Fiber | 60676-86-0 | 50–90 | 5 mg/m$^3$/ 15 mg/m$^3$ (Respirable/ Total dust) | 10 mg/m$^3$ (Fibrous Glass) | See Health Effect |
| Silicon Carbide | 409-21-2 | 1–3 | 5 mg/m$^3$/ 15 mg/m$^3$ (Respirable/ Total dust) | 10 mg/m$^3$ (Total nuisance dust) | |
| Boron Nitride | 10-043-115 | 1–5 | 5 mg/m3/ 15 mg/m3 (Respirable/ Total dust | 10 mg/m3 (Total nuisance dust) | |

III. Physical Properties

Vapor density (air = 1): NA
Specific gravity: Varies
Solubility in water: Nil
Vapor pressure, mmHg at 20 degrees c.: NA
Evaporation rate (butyl acetate = 1): NA
Appearance and odor: Solid off-white blocks, no odor.
Softening point or range, degrees F.: 2876
Boiling point or range, degrees F.: NA Also, a reusable surface insulation (HRSI) is described by a Lockheed Missles & Space Co. Fact Sheet, released September, 1988, titled, *Thermal Protection System* (incorporated herein by reference)

Cell Growth in Implants

Implants for drug delivery and infection control preferably interact with the organism in which they are implanted, the interaction being through the medium of tissue fluid and by cellular contact with the implant. The extent of angiogenesis and cellular growth within the implant and the distance through which materials from the implant must diffuse through the tissue fluid to reach the organism's circulatory system may have important effects on functioning of the implant. The latter parameter is especially applicable in the case of implants for drug delivery.

Applications for Drug Delivery Implants

Administration of one or more drugs to a patient at predetermined dosage rates is required for effective treatment and/or prevention of several infectious diseases, including, e.g., tuberculosis, malaria and certain sexually-transmitted diseases (STD's). Public health measures adopted to cope with these diseases rely heavily on administration of prophylactic and treatment drugs on an outpatient basis, but the rising incidence and prevalence of infectious diseases in certain populations (e.g., homeless or medically indigent families and migrant workers) reflect the limited efficacy of current treatment and prevention programs in such groups.

The success of outpatient treatment and prevention programs depends substantially on each patient's compliance with prescribed dosage(s) to achieve and maintain therapeutic or prophylactic drug levels. Deviation from a predetermined dosage rate or duration may result in a relapse or exacerbation of the disease at issue. In particular, a patient's premature termination of orally administered drug treatment can allow the survival and proliferation of drug-resistant microorganisms, as has occurred in patients having tuberculosis and STD's such as gonococcal salpingitis.

Patients infected with relatively drug-resistant pathogens become progressively more difficult and expensive to treat. Those not treated or inadequately treated act as reservoirs of disease. They easily infect or reinfect those with whom they have contact, and thus constitute a significant public health threat. Especially within transient populations and those living in crowded public accommodations, infectious diseases will continue to be passed back-and-forth unless the chain of transmission is broken through effective treatment of infectious patients. One means of providing such treatment involves providing effective drug therapy through systems for controlled or delayed drug release in vivo. In patients who present repeatedly with the same disease and who either can not or will not comply with an oral dosage regimen, implants which operate automatically to provide therapeutic drug levels in vivo may reasonably be offered as part of effective therapy.

Existing Implantable Drug Delivery Systems

A variety of implantable drug delivery systems already exist for controlled release of drugs in vivo over prescribed periods of time. Examples include: (1) systems comprising drugs encapsulated in non-biodegradable membranes, e.g., levonorgestrel in flexible closed capsules made of SILASTIC® brand dimethylsiloxane/methylvinylsiloxane copolymer (the NORPLANT® system); (2) drugs prepared in relatively insoluble form for intramuscular, intra-articular or subcutaneous injection, e.g., penicillin G benzathine and penicillin G procaine (BICILLIN® C-R), methylprednisolone acetate aqueous suspension (DEPO-MEDROL®), or norethisterone dispersed in poly (DL lactide-co-glycotide) microcapsules; and (3) drugs dispersed in formed biodegradable implants, the implants comprising, e.g., polyhydroxybutyrate with or without hydroxyapatite. All of these systems, however, are associated with significant disadvantages.

Encapsulated drug norms intended for implantation, as in the NORPLANT* system, are subject to errors in placement which may cause capsule expulsion and consequent irregularities in drug delivery rate. Capsules may also be difficult to remove, but can not be left in place indefinitely (it is recommended that all capsules be removed after five years).

Additionally, intramuscular, intra-articular or subcutaneous injections of drugs such as BICILLIN® C-R, DEPO-MEDROL® or norethisterone are painful, and patients may tend to delay or avoid treatments involving repeated injections due to the expected discomfort. Furthermore, the rate of drug delivery from subcutaneous dosage forms is substantially limited by the local blood supply.

Finally, formed implants of biodegradable polyester, even when reinforced with hydroxyapatite, tend to experience significant declines in elastic modulus and bend strength after weeks to months of implantation. The resulting tearing and cracking of the implant can then alter the amount of implant surface exposed to body fluids and cellular activity, which in turn may cause unpredictable changes in the delivery rate of any drug(s) dispersed within the implant. Because stability and predictability of drug administration rates are paramount considerations, implants containing brittle materials or drug deposits should ideally retain their shape and strength during the entire course of implantation and even after depletion of the administered drug. High levels of shape and strength retention would also facilitate changes in the drug administration regimen and would also allow removal of the implant at the convenience of the patient rather than on a fixed schedule.

In view of the disadvantages summarized above for currently available implantable drug delivery systems, a more flexible and reliable implantable system for drug delivery is needed. Changes in the drug treatment regimen (i.e., drug selection and dosage rate) should be relatively easily made and easily changed, and communication between the implant and the local tissue into which it is implanted should be controllable throughout the life of the implant through selective stimulation of cell growth and angiogenesis from the local tissue to the implant. At the present time, no system combining these desired characteristics is commercially available.

Implants for Infection Control

The functions described above as useful in implants for drug delivery would also be useful in implants for infection control, as where a break occurs in the skin at a site of percutaneous catheter insertion. Implants currently used in such applications frequently comprise one or more fibrous cuffs for interface with the body tissues, but the cuffs themselves may become infected because normal immune responses are impeded in the area of the implant. Catheter-related infections may thus be reduced by improved communication between the cuff implant and the local tissue. As in the case of implants for drug delivery, functional integration of the cuff implant with surrounding tissue would preferably be controllable throughout the life of the implant by selective stimulation of cell growth and angiogenesis from the local tissue to the implant. Implantable cuffs facilitating such control are not, however, commercially available.

SUMMARY OF THE INVENTION

Implants for drug delivery and infection control (infection shields) according to the present invention substantially avoid the shortcomings of prior implants noted above by incorporating an implantable system for cell growth control as described herein. Each drug delivery implant of the present invention comprises a porous linked fibrous biomaterial drug reservoir, the voids of which, in some embodiments, contain one or more drugs which may be dispersed within a biodegradable matrix. Cell growth and angiogenesis within the reservoir is controlled and directed as described herein. Note that drugs to be delivered, as well as the matrix materials (if present), may include metabolic products of the organism in which a drug reservoir is intended to be placed, or of other organisms.

In other embodiments, a cuff-shaped infection shield inhibits the passage of pathogenic microorganisms along a catheter or other percutaneously implanted device through control of cell growth and angiogenesis within the shield as described herein. Further embodiments include a reservoir having one or more sealable interior chambers containing cultured living cells which can communicate through porous chamber walls, by the medium of tissue fluid and/or cell growth medium, with cells of the organism in which the reservoir may be implanted or with an external fluid exchange system (as in a bioreactor). Infection shielding cuffs or reservoir implants according to the present invention both comprise fibrous biomaterials which are biocompatible. As described herein, biocompatible implants support controlled cell growth and angiogenesis within an organism while not evoking a foreign body immune response which significantly adversely affects preferred implant function.

Implant biomaterials may be biodegradable (i.e., they may dissolve in tissue fluid to form nontoxic solutions), or they may be substantially non-biodegradable (e.g., silica fibers).

Implantation of infection shields and drug reservoirs of the present invention is preferably carried out in vascular tissue of an organism. Vascular tissue is tissue which contains circulatory system vessels (including lymphatic and blood vessels) and tissue fluid in sufficient quantity to sustain cells growing within the implant and to transport drug released from a reservoir implant to the circulatory system vessels.

Drug transport may be by diffusion, convection, or facilitated diffusion. In reservoirs which contain cell cultures and are implanted within vascular tissue, food and oxygen diffuse toward the cultured cells and metabolic products (including one, or more desired drugs) diffuse away from them via the tissue fluid. Similarly, cells invading the implant from the local tissue of the organism are sustained through exchange of food, oxygen and metabolic products with circulatory system vessels growing within the implant from the local tissue.

In all embodiments of the present invention, a reservoir or infection shield implanted in vascular tissue tends to: (1) retain the desired implant shape and structural integrity for a duration of implantation which substantially exceeds the planned duration of implantation for the shield or the duration of drug administration from a reservoir implant, and (2) aid in sustaining cells growing within the implant and/or coupling drugs emanating from the reservoir to the circulatory system for timely delivery of effective drug doses to one or more desired sites of action within the organism. Each implant embodiment reliably performs these functions over periods of implantation from a few days to several months, depending on its design. Note that the tendency for embodiments of the present invention to retain is a desired implant shape does not preclude flexible implants according to the present invention (e.g., implants in the form of a flexible sheet). In such implants, flexibility does not substantially degrade the functions of stimulation of cell growth and angiogenesis, and/or support of cultured cells within the implant.

Drug reservoirs and infection shields in all embodiments of the present invention comprise relatively non-biodegradable fibrous biomaterials linked at fiber intersections to aid in substantially retaining their shape after prolonged implantation. Shape retention includes retention of the mechanical integrity of any cell culture or biodegradable matrix which may be present, i.e., substantial disruption of the cell spacing and matrix fragmentation are avoided for at least the useful life of the implant. The fiber linking which facilitates shape retention includes processes capable of substantially maintaining the spatial relationship of one fiber with respect to other fibers which touch it for the effective life of an implant comprising the fibers. Process examples include fusing (e.g., with silica fibers), chemical bonding (e.g., with polymer fibers), and adhesion (e.g., with colloidal silica). Additionally, and notwithstanding their relatively non-biodegradable porous linked fibrous biomaterial component, reservoirs and infection shields of the present invention are substantially biocompatible.

Angiogenesis in the Implant

In particular, implant biocompatibility is reflected both in the ability to stimulate and sustain populations of cells within the implants, and in the function of coupling drugs which emanate from within a reservoir to the circulatory system of the organism in which the reservoir is implanted. Within portions of implants intended to either sustain cultured cells or stimulate angiogenesis or cell growth from adjacent vascular tissue, the implant material substantially hydrophilic and contains mean pore (void) sizes and porosities which have been empirically determined to support the desired function of the implant.

Angiogenesis within the implant helps ensure that it is functionally integrated within the circulatory system of the patient into which the implant is placed. The controlled and progressive nature of angiogenesis and cell growth into implants differentiates implantable infection shields and systems for drug delivery of the present invention from all prior devices, systems and methods.

Cell growth in general and angiogenesis in particular within implants of the present invention is a function of the mean void size, fiber composition and surface chemical characteristics of the biomaterial fibers. In implants comprising fibrous biomaterials of substantially uniform fiber size range and fiber distribution, implant density is substantially inversely related to void or pore size. For example, implants comprising Q-Fiber® (amorphous high purity silica) obtained from the Manville Division of Schuller International Inc., Waterton, Ohio, and prepared as described herein at high density (39 pounds/cubic foot) support approximately ⅓ the cell growth of similar material prepared at a low density of 12 pounds/cubic foot). Hence, areas of high and low cell growth potential may be incorporated in an implant by making the respective portions of low and high density material. To achieve the desired ratio of high/low cell growth potential, one need only perform in vitro tests using cells of the tissue in which implantation is desired or cells of the type desired to be cultured. Preferred high and low density values for sections of an implant which are to respectively inhibit or support cell growth may thus be determined. Note that in other preferred embodiments of the present invention, conditions of high and low cell growth potential may be achieved at least in part by alterations in fiber surface composition and/or coatings, in addition to or in place of density alterations.

In any embodiment of the present invention, it is preferable that initial implant densities (ignoring any matrix which may be present) remain substantially unchanged throughout the useful life of the implant. Such consistency of density may be achieved through linking of the biomaterial fibers comprising the implant. Linking acts to maintain the range of void or pore sizes necessary for proper functioning of the implant. The degree of linking and the degree of flexibility at individual linkages required will be empirical functions of the fiber type chosen and the strength requirements of the particular implant configuration chosen (e.g., elastic modulus, bending strength).

Composition and Function of a Biodegradable Matrix

Within reservoirs of certain preferred embodiments of the present invention, one or more treatment or prophylaxis drugs are dispersed within a matrix, the matrix being dispersed within the pores (voids) of the linked fibrous biomaterial. The matrix comprises one or more biodegradable biomaterials, the exact composition being determined by the desired rate and duration of matrix biodegradation (with its resultant drug release). Note that drugs may be microencapsulated prior to dispersion within the matrix to further delay their release in active form and/or to reduce the concentration of free drug in the immediate vicinity of the reservoir.

Suitable materials for the biodegradable matrix include but are not limited to homopolymers (e.g., poly-paradioxanone, polylysine or polyglycolic acid) and copolymers (e.g., polylactic acid and polyglycolic acid). Biodegradable polymers may be augmented in the matrix (or even replaced, in certain embodiments) by non-biodegradable biomaterials, including but not limited to, e.g., Glassfiber®, plaster of Paris, beta-whitlockite, hydroxyapatite, and various other calcium phosphate ceramics.

Structure and Function of the Implant

In all embodiments of the present invention comprising a matrix, the porous linked fibrous biomaterial tends to establish and maintain the physical characteristics of the implant (and any matrix or drug contained therein), and to direct newly-formed blood vessels thereto, i.e., acting to control the number and location of the newly-formed blood vessels within the implant. Implants which contain a biodegradable matrix acquire new and/or larger voids as the matrix is removed through the action of tissue fluid. Thus, there is within the implant a changing level and location of angiogenesis and new cell growth as portions of the matrix are biodegraded.

Such local direction of cell growth and blood vessel proliferation effectively controls and directs the implant integration and biodegradation processes. Similarly, the rate of absorption of cell culture metabolic products in implants containing cultured cells is also regulated.

For embodiments employing cell cultures, diffusion distance from the cultured to the circulatory system may remain substantially unchanged after initial angiogenesis within the reservoir. For drug or matrix-containing embodiments on the other hand, the diffusion distance from matrix to circulatory system will in general be constantly changing.

If desired, the effective mean distance over which matrix components (including drugs) must diffuse to reach the circulatory system can be maintained substantially constant throughout the life of the present implant. As matrix components are dissolved and carried away by first the tissue fluid and then the blood stream, angiogenesis results in the effective repositioning of the circulatory system closer to the remaining (undissolved) matrix. Angiogenesis, in turn, is controlled by several factors including, but not limited to: void size in the reservoir, reservoir porosity, and the composition of the reservoir's linked fibrous biomaterial.

Angiogenesis may be encouraged or inhibited at a particular location within the implant because it is effectively directed by the communicating voids of the implant only if the voids are within an empirically predetermined preferred size range. Voids either too large or too small will substantially inhibit or even prevent angiogenesis. On the other hand, voids within a preferable size range will stimulate extension of the circulatory system with the implant.

In embodiments of the present invention having a biodegradable matrix, new voids are formed continuously by dissolution of the biodegradable matrix; actual void size progressively increases toward the limit allowed by the reservoir structure. In contrast, in embodiments without a matrix, the voids present initially on implantation are those characteristic of the linked fibrous biomaterial. In either type of embodiment, however, drug absorption by the circulatory system can be made to proceed in an orderly and substantially predictable manner.

In matrix-containing embodiments, drug absorption at substantially predetermined rates occurs often as the shape and size of the biodegradable matrix mass changes. No prior drug delivery systems operate in this manner to ensure a controlled blood flow adjacent to a drug-producing or drug-storing implant, even when a drug storage element (i.e., the matrix) is itself a changing biodegradable moiety.

Effects of Implant Porosity

Note that while voids of the proper size will tend to stimulate angiogenesis in certain areas of the implant, the porosity of the linked fibrous biomaterial will ultimately limit the to total blood flow per unit volume of the reservoir. Porosity is defined as the percent of void space relative to a given volume of linked fibrous biomaterial material in the implant (ignoring any matrix which may be present). Because an increase in porosity tends to allow an increase in the total amount of blood flow in the implant (through angiogenesis), it also tends to decrease the mean diffusion distance separating blood vessels from cultured cells or biodegradable matrix components within the implant.

Conversely, decreasing the porosity of the reservoir tends to increase the mean diffusion distance. Thus, the choice of preferred porosity for any reservoir (or portion thereof) will depend on the desired density of tissue ingrowth or the flux of drug desired from the implant. For example, relatively high drug flux values would ordinarily be desirable for implants delivering antibiotics, while relatively low drug flux values would be needed for delivery of hormones.

Note that the amount of drug flux needed from a given implant may be influenced by placement of the implant. Proper choice of an implantation site may result in relatively higher drug concentrations in certain regions of the body where the drug is most needed, thus perhaps allowing lower average blood levels of the drug.

Cell Isolation by Channel Size Control

An important aspect of the structure of infection shield implants and reservoir implants intended to contain cultured cells is the presence of channels for tissue fluid which are too small for cell or vessel growth but large enough to allow effective diffusion of food, oxygen and metabolic products between cells and vessels. Such channels can effectively isolate interior portions of a reservoir from contact with the host organism except through the medium of tissue fluid components which pass through them. Similarly, such channels can inhibit the passage of microorganisms through an infection shield while supporting growth of skin or subcutaneous tissue into other portions of the shield.

In preferred embodiments of the present invention containing cultured cells, channels within portions of the reservoir intended to support angiogenesis from the host organism will adjoin the porous wall of a sealable inner chamber of relatively dense porous linked fibrous biomaterial. The chamber wall, which is preferably relatively thin, effectively separates host organism cells and new blood vessels formed in the reservoir from the cultured cells, except for communication through tissue fluid channels in the porous chamber wall. Mechanical support for the thin chamber wall is provided by linked biomaterial fibers which, in a less-dense linked pattern, comprise the remaining structure of the reservoir. Preferred density ranges for each reservoir material and cultured cell type are empirically determined by in vitro testing.

Implant Placement

Infection shield embodiments of the present invention are preferably placed around a percutaneously-placed object (e.g., a catheter) at or near the point where the object passes through the skin and subcutaneous tissue. In certain embodiments, the shield comprises a substantially cylindrically shaped catheter seal for substantially circumferentially surrounding the catheter, the seal comprising porous linked fibrous biomaterial (e.g. silica fiber) having a plurality of voids of a predetermined mean void size effective for inhibiting angiogenesis from the skin and subcutaneous tissue, and a tissue cuff circumferentially surrounding the catheter seal, the cuff comprising porous linked fibrous biomaterial having a plurality of voids of a predetermined mean void size effective for stimulating angiogenesis in the cuff from the skin and subcutaneous tissue.

Tissue ingrowth with attendant angiogenesis links the skin and subcutaneous tissue with the implant. Such ingrowth is preferably stopped adjacent to the object by a layer of relatively dense linked fibrous biomaterial which substantially blocks further tissue ingrowth and angiogenesis, but which does not provoke a foreign body response from the organism in which the shield is implanted. Thus, passage of pathogenic organisms around the percutaneously-placed object is effectively blocked by the ingrowth of tissue, and infection is prevented. This type of implant placement differs substantially from that preferred for drug delivery systems.

Drug delivery implants of the present invention are preferably placed within or adjacent to vascular tissue. Such tissue offers an appropriate base from which angiogenesis from the tissue to within the reservoir (characteristic of all embodiments after implantation) may proceed. Two preferred locations for implantation are within the marrow of long bones and within a surgically constructed peritoneal pouch.

One alternative method of reservoir placement within bone is to secure the reservoir itself with external fixation in a manner similar to that used for fixation of bone fractures. Reservoirs of the present invention may be shaped to fill existing bony defects (e.g., missing bone due to injury), and one or more drugs to stimulate osteogenesis (e.g., transforming growth factor beta, osteogenin and osteocalcin) may, for example, be dispersed within the matrix. Reservoirs for applications requiring external fixation would typically comprise relatively high-strength biomaterial fibers and relatively high levels of linking at fiber crossings. Such reservoirs would biodegrade relatively slowly over time as the strength required of the reservoir is increasingly provided by newly formed bone within the voids of the reservoir.

Another alternative method of reservoir implantation in bone requires installation of a permanent fixture within the bone. The fixture allows ready access to the implant and frequent, substantially atraumatic changes of the reservoir. The general design of such a fixture is suggested by reference number 12 in U.S. Pat. No. 4,936,851 (Fox, et al.), incorporated herein by reference. A fixture of this general design can be allowed to become a substantially permanent part of the bone in which it is placed (using methods for implantation and subsequent wound care similar to those described in Fox, et al.).

After implantation, the fixture may accommodate one or more substantially cylindrically shaped reservoirs of the present invention. Properly-shaped fenestrations in the fixture wall (see reference number 15 of Fox, et al. for an example of one type of fenestration) allow angiogenesis of the porous linked fibrous biomaterial of the reservoir(s). Note that stacking of two or more substantially cylindrical reservoirs in a fixture implanted in bone is a preferred method of simultaneously providing more than one drug, or providing a single drug having more than one desired flux level over time, to an organism by using devices of the present invention. A desired ratio of the drugs provided may be easily achieved through appropriate choice of the lengths and/or drug release capacities of reservoirs inserted in the fixture. Similarly, drug combinations and ratios are easily changed through replacement of an existing set of implanted reservoirs (or portions thereof) with another set.

Note also that substantially cylindrical reservoirs for delivery of different drugs, for delivery of the same drug at different rates, can be cut into a variety of differing forms, with pieces from different reservoirs being reassembled into a substantially cylindrical form suitable for insertion into a fixture. Such a mosaic reservoir may provide a variety of drug dosage profiles over time, as may be required in certain drug treatment and prophylaxis protocols.

Access to the fixture through a small skin incision and a fixture cap (see reference number 14 of Fox, et al. for an example of one type of fixture cap) could be substantially as described in Fox et al. Removal of a cylindrically shaped reservoir from a fixture in which it has become substantially integrated with both the bone tissue and circulatory systems of the bone marrow may be accomplished through a process analogous to trephination. Fox, et al. does not describe a separate trephine tool, but methods and devices for trephination are well known to those skilled in orthopedics and neurosurgery.

For implants of the present invention having a longer projected life, or those in which implantation in the abdominal cavity is desired, implantation of reservoirs in a peritoneal pouch created by open or endoscopic surgery may be desirable. By totally enclosing each implant in a peritoneal cover, substantial potential for angiogenesis is provided, while the likelihood of adhesion formation between the external surface of the pouch and adjacent structures is minimized.

Preparation of Porous Linked Fibrous Biomaterial Reservoirs

Porous linked fibrous biomaterial reservoirs of the present invention do not have a fixed composition. They are relatively non-biodegradable for the functional life of the implant, retaining sufficient mechanical strength to maintain porosity values and void size consistent with the degree of angiogenesis desired in the reservoir. In certain preferred embodiments (e.g., for insertion in and subsequent removal from fixtures in bone), they preferably comprise nonwoven, randomly oriented, high-purity silica fibers which are linked at a plurality of crossing points into a substantially non-biodegradable porous structure. In other preferred embodiments (e.g., for one-time delayed-release drug administration), a reservoir may preferably comprise linked Glassfiber® which will retain its shape until the reservoir drug is exhausted or until any cultured cells within the reservoir become non-viable.

A general method for making linked fibrous silica is described in U.S. Pat. No. 3,952,083 (Fletcher, et al.), which is incorporated herein by reference. Alterations of the method of Fletcher, et al. to make the porous linked fibrous biomaterial of the present invention are evident in the manufacturing protocol provided in the Detailed Description given below.

DETAILED DESCRIPTION

Implantable infection shields and systems for drug delivery according to the present invention comprise porous linked fibrous biomaterial disposed to either stimulate or inhibit cellular growth and/or angiogenesis, according to the predetermined requirements of the various embodiments.

One embodiment is a reservoir which contains within it a source of one or more drugs to be delivered. Intended for implantation in vascular tissue, the drug source may be a biodegradable matrix in which the drug or drugs to be delivered are dispersed, and which dissolves slowly in tissue fluid from the organism in which the reservoir is implanted. The source may also be a cell culture contained within a sealable porous chamber within the reservoir. Cultured cells receive food and oxygen by diffusion in the tissue fluid which passes through the sealable porous chamber walls. Cell-to-cell contact between cells of the organism and cultured cells is, however, prevented.

Thus, a method for making a system for drug delivery for implantation in vascular tissue, the method comprises obtaining a reservoir comprising porous linked fibrous biomaterial having a plurality of voids of a predetermined mean void size effective for stimulating angiogenesis in said reservoir from the vascular tissue, providing a biodegradable matrix, dispersing a drug to be delivered in said biodegradable matrix to form a drug delivery matrix, and dispersing said drug delivery matrix within said voids to make a system for drug delivery.

Figures 1, 2:
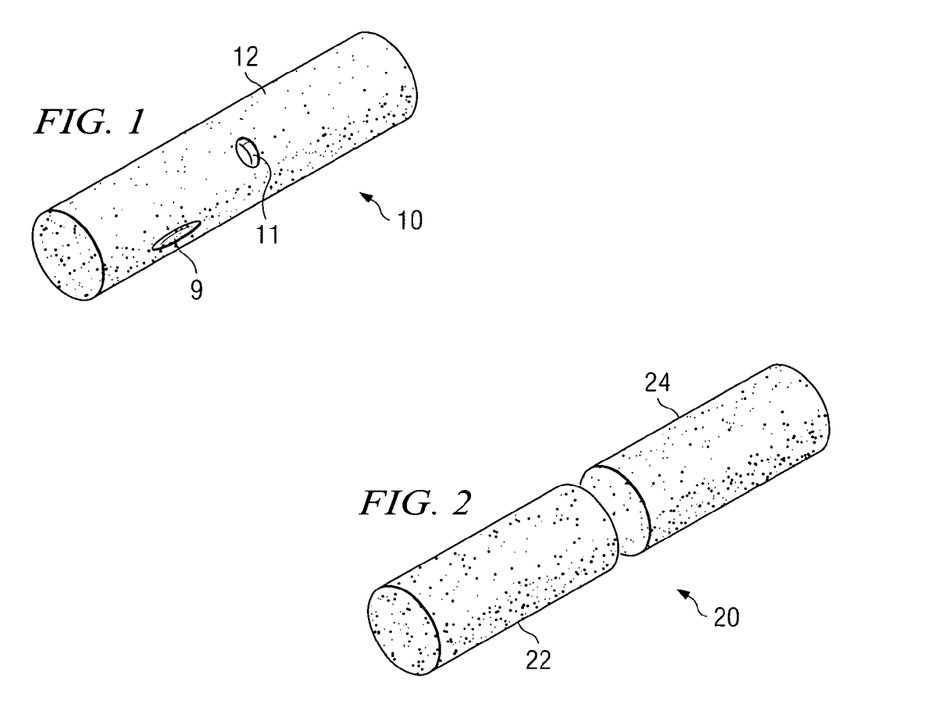
FIG. 1 illustrates a cylindrically shaped reservoir for insertion in a fixture in bone.
FIG. 2 illustrates two cylindrical reservoirs of differing composition intended for simultaneous insertion in a fixture in bone.

FIG. 1 illustrates a preferred embodiment of a reservoir 10 comprising porous linked fibrous biomaterial 12, according to the present invention; the reservoir 10 is suitable for insertion into a fixture in a bone analogous to reference number 12 in U.S. Pat. No. 4,936,851 (not shown). The reservoir 10 may also be inserted directly in vascular tissue (e.g., breast tissue), and the reservoir surface area may be increased by changing its shape (e.g., by flattening it) or by perforating the reservoir 10 with one or more holes 11 or depressions 9.

FIG. 2 illustrates two reservoirs 22,24 similar to the reservoir 10 in FIG. 1, except that they are intended for simultaneous insertion into a fixture in a bone (not shown). Together, the two reservoirs 22,24 comprise a new reservoir 20 which may serve as the source of two different drugs, reservoir 22 providing one drug and reservoir 24 providing the other. Note that the reservoirs 22,24 may also provide the same drug, but at differing rates and for differing durations. Simultaneous insertion of reservoirs 22,24 then allows the new reservoir 20 to provide a drug at a rate which varies with time. Note that in a manner analogous to that shown in FIG. 2, a plurality of drugs may be provided in fluxes having predetermined ratios to one another through simultaneous insertion of appropriate drug reservoirs in one or more fixtures in bone.

Figure 3:
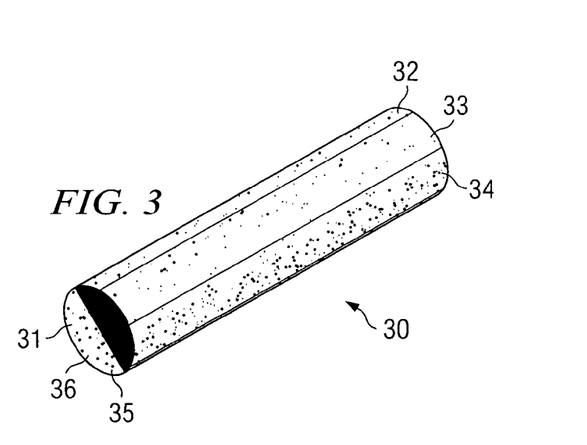
FIG. 3 illustrates a cylindrical reservoir having longitudinal cylindrical segments; each segment may have a different composition.

FIG. 3 illustrates another form of reservoir 30 which may act as a source for each of the drugs contained within longitudinal cylindrical segments 31–36. The reservoir 30 may also be inserted in a fixture in a bone as noted above (not shown).

Figure 4A:
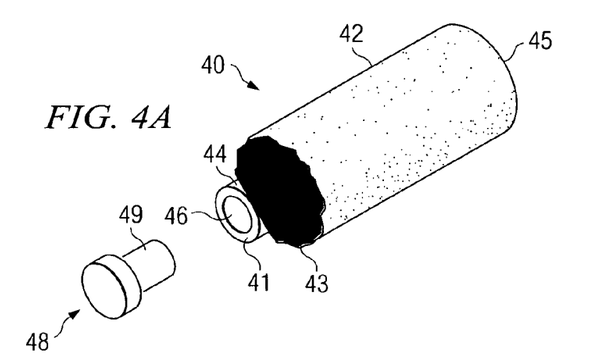
FIG. 4A illustrates a reservoir suitable for cell culture and for insertion in a fixture in bone.
Figure 4B:
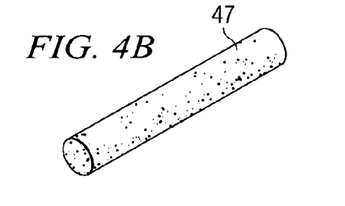
FIG. 4B illustrates a void insert of linked fibrous biomaterial intended for use with the reservoir of FIG. 4A.

FIG. 4A illustrates a reservoir 40 of the present invention intended to contain a cell culture (not shown) and for coupling the cell culture to vascular tissue (not shown) in which the reservoir may be implanted. A cell culture may be contained within a sealable interior chamber, the wall 44 of which is illustrated. The chamber wall 44 is sealed at end 45 but is shown open at end 41. Chamber wall 44 comprises porous linked fibrous biomaterial having a plurality of voids of a predetermined mean void size effective for inhibiting angiogenesis in chamber wall 44 from the vascular tissue in which reservoir 40 is intended to be implanted. Cultured cells may be inserted within central void 46 within chamber wall 44, and then sealed therein by inserting plug 49 of cap assembly 48 within central void 46. Outer coat 43 comprises porous linked fibrous biomaterial having a plurality of voids of a predetermined mean void size effective for stimulating angiogenesis in reservoir 40 from the vascular tissue in which reservoir 40 is intended to be implanted. Note that for clarity in FIG. 4A, outer coat 43 is shown cut back from chamber wall 44. In preferred embodiments of the present invention, outer coat 43 is not cut away as shown in FIG. 4A, but instead substantially completely surrounds chamber wall 44. Note also that cultured cells (not shown) within central void 46 may preferably grow by layering on the surface of chamber wall 44 which faces central void 46. Cultured cells may also preferably grow within and on void insert 47 (illustrated in FIG. 4B) if insert 47 is placed within void 46 prior to sealing with plug 49 of cap assembly 48. Insert 47 comprises porous linked fibrous biomaterial having a plurality of voids of a predetermined mean void size effective for stimulating growth and/or differentiation of cultured cells.

Figure 5A:
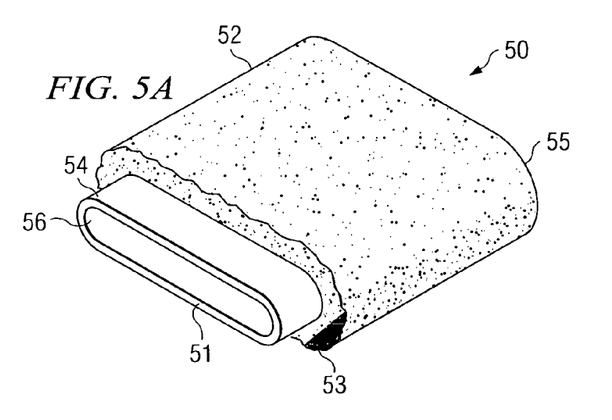
FIG. 5A illustrates a reservoir suitable for cell culture and for implantation in a peritoneal pouch.

FIG. 5A illustrates a reservoir 50 which is analogous to reservoir 40 in FIG. 4A except that it provides a larger ratio of area of chamber wall 54 to volume of central void 56. Other shapes (not illustrated) for chamber wall 54 might also be chosen for certain embodiments (e.g., a substantially cubic shape). A reservoir having a shape analogous to that of reservoir 50 may, for example, be preferred for implantation in a peritoneal pouch. If reservoir 50 is used in a bioreactor application, the reactor would preferably comprise a plurality of reservoirs 50 held in spaced relationship within surrounding fluid growth medium and/or tissue fluid.

Figure 5B:
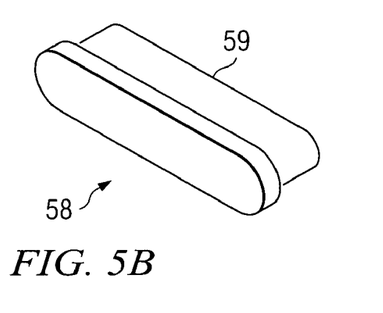
FIG. 5B illustrates a cap assembly for occluding the cell culture cavity of the reservoir of FIG. 5A.
Figure 5C:
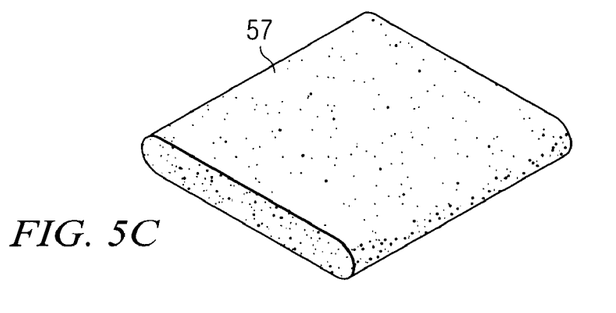
FIG. 5C illustrates a void insert of linked fibrous biomaterial intended for use with the reservoir of FIG. 5A.

A cell culture may be contained within a sealable inner chamber of reservoir 50, the wall 54 of which is illustrated. The chamber wall 54 is sealed at end 55 but is shown open at end 51. Chamber wall 54 comprises porous linked fibrous biomaterial having a plurality of voids of a predetermined mean void size effective for inhibiting angiogenesis in reservoir 50 from the vascular tissue in which reservoir 50 is intended to be implanted. Chamber wall 54 also acts to prevent cultured cells from passing through the wall 54. Cultured cells may be inserted within central void 56 within chamber wall 54, and then sealed therein by inserting plug 59 of cap assembly 58 (see FIG. 5B) within central void 56. Outer coat 53 comprises porous linked fibrous biomaterial having a plurality of voids of a predetermined mean void size effective for stimulating angiogenesis in reservoir 50 from the vascular tissue in which reservoir 50 is intended to be implanted. Note that in bioreactor applications, outer coat 53 acts to provide mechanical strength to the relatively thin chamber wall 54. Note also that for clarity in FIG. 5A, outer coat 43 is shown cut back from chamber wall 54. In preferred embodiments of the present invention, outer coat 53 is not cut away as shown in FIG. 5A, but instead substantially completely surrounds chamber wall 54. Note also that cultured cells (not shown) within central void 56 may preferably grow by layering on the surface of chamber wall 54 which faces central void 56. Cultured cells may also preferably grow within and on void insert 57 (illustrated in FIG. 4C) if insert 57 is placed within void 56 prior to sealing with plug 59 of cap assembly 58. Insert 57 comprises porous linked fibrous biomaterial having a plurality of voids of a predetermined mean void size effective for stimulating growth and/or differentiation of cultured cells.

Figure 6:
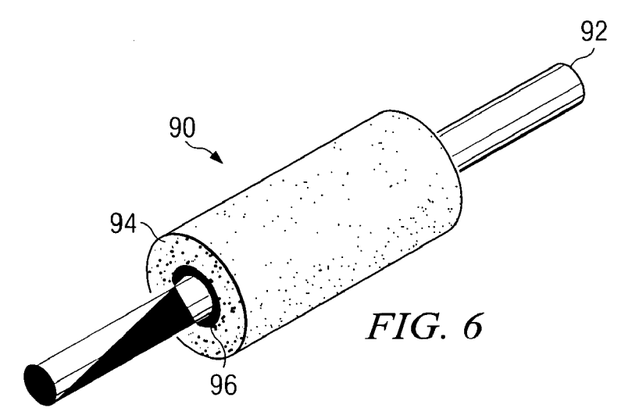
FIG. 6 illustrates an infection shield applied around a catheter.

FIG. 6 illustrates an infection shield 90 for a catheter intended for placement through skin and subcutaneous tissue according to the present invention; shield 90 is shown applied around a catheter 92. Infection shield 90 comprises a catheter seal 96 and a tissue cuff 94. Catheter seal 96 comprises substantially cylindrically shaped porous linked fibrous biomaterial (e.g., silica fiber) for substantially circumferentially surrounding a catheter, the seal 96 having a plurality of voids of a predetermined mean void size effective for inhibiting angiogenesis from the vascular tissue which may contact infection shield 90. Tissue cuff 94 comprises porous linked fibrous biomaterial (e.g., silica fiber) having a plurality of voids of a predetermined mean void size effective for stimulating angiogenesis in cuff 94 from the skin and subcutaneous tissue in which infection shield 90 and catheter 92 might be implanted. Tissue cuff 94 substantially circumferentially surrounds catheter seal 96. In use, catheter seal 96 of infection shield 90 substantially circumferentially surrounds a catheter 92.

Protocol for Manufacturing Porous Linked Fibrous Silica Fiber

Figure 7:
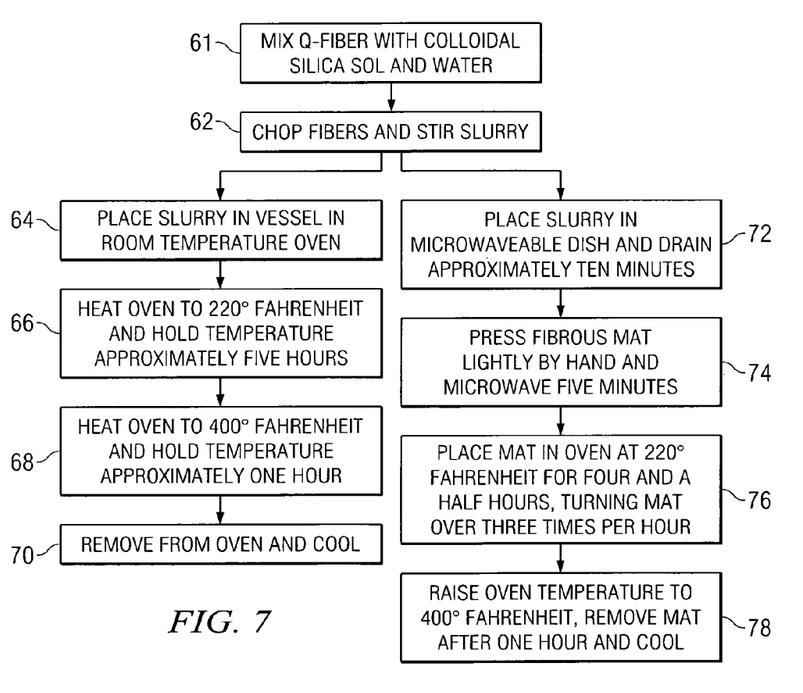
FIG. 7 is a block diagram of a process to make linked silica fiber according to the present invention.

The process for manufacturing linked silica fiber comprises preparation of a silica fiber slurry, followed by heat treatment of the slurry. Either a substantially rough or a partially smooth outer surface may be produced on the porous linked silica fiber, depending on the heat treatment used on the slurry. A flow diagram representing the process is illustrated in FIG. 7.

In step 61, 60g of Q-Fiber® (amorphous high purity silica fiber), Manville Division of Schuller International, Inc., Waterton, Ohio, is added to 1000 ml of "Nyacol 1430" (colloidal silica sol), PQ Corporation, Ashland, Mass. and distilled water (1 part Nyacol plus 9 parts water) in a stainless steel container ("VitaMixer Maxi 4000 from Vita-Mix Corporation, Cleveland, Ohio). Note that the above dilution produces porous linked fibrous biomaterial according to the present invention at a density of approximately 12 pounds per cubic foot, whereas if the silica sol is used undiluted, the density will approximate 39 pounds per cubic foot.

In step 62, the mixture is stirred for two minutes with a rotating blade to chop the fibers and create a homogeneous slurry. To make a linked silica fiber with one smooth outer surface and one rough surface, steps 64, 66, 68 and 70 are executed as follows. In step 64, approximately one hundred milliliters of the slurry is poured into a Pyrex vessel (20 cm×20 cm by 6 cm). Contact between the slurry and the Pyrex surface is preferably prevented by a thin membrane placed over the Pyrex surface (e.g., Teflon®). The vessel is placed in an oven at room temperature. In step 66, the oven is heated to about 220 degrees Fahrenheit within approximately 5 minutes and remains at this temperature for approximately 5 hours. In step 68, the oven temperature is then raised to about 400 degrees Fahrenheit in approximately 10 minutes and remains at this temperature for approximately 1 hour.

In step 70, a sheet is removed from the oven and cooled, the sheet being a piece approximately 1 to 2 mm thick by approximately 20 cm×20 cm of linked fiber, the piece having a bottom side (which was against the Pyrex dish) that is smooth and shiny and a top side (exposed to the air) that is relatively rough. The shiny side is apparently a homogeneous layer of deposited silica integrated into the linked fiber matting. The shiny and rough sides are both previous to water and hydrophilic in character.

To make a porous linked silica fiber with a continuous rough surface overall, steps 72, 74, 76 and 78 in FIG. 7 are executed as follows. In step 72, approximately 680 ml of the slurry prepared above in step 62 is poured into a plastic microwaveable dish 9.5×3.5×6 cm with 12 holes 0.2–0.4 cm in diameter in the bottom of the dish. The liquid of the slurry is allowed to drain through the holes over about 10 minutes. In step 74, the fibrous mat is pressed lightly by hand using a plastic form mold piston, after which the mat is heated for 5 minutes in a microwave oven.

In step 76, the mat is transferred in a Teflon®-lined pan to an oven at approximately 220 degrees Fahrenheit. The mat is turned over three times every hour. The temperature is maintained for about four and one-half hours. In step 78, the oven temperature is raised to approximately 400 degrees Fahrenheit, and the linked fiber block is removed after about 1 hour and allowed to cool; all six sides of the cooled linked fiber block are rough.

Protocol for Manufacturing Porous Fused Rigid Ceramic

One process for manufacturing fused silica/alumina and/or other ceramic fiber of low density, like 12 lb. per ft.$^3$, comprises:

(1) preparation of a slurry mixture comprised of pre-measured amounts of purified fibers and deionized water;

(2) removal of shot from slurry mixture;

(3) removal of water after thorough mixing to form a soft billet;

(4) addition of a ceramic binder after the formation of the billet;

(5) placement of the billet in a drying microwave oven for moisture removal; and (6) sintering the dry billet in a large furnace at about 1600° F. or above.

The high purity silica fibers above are first washed and dispersed in hydrochloric acid and/or deionized water or other solvent. The ratio of washing solution to fiber is between 30 to 150 parts liquid (pH 3 to 4) to 1 part fiber. Washing for 2 to 4 hours generally removes the surface chemical contamination and non-fibrous material (shot) which would contribute to silica fiber devitrification. After washing, the fibers are rinsed 3 times at approximately the same liquid to fiber ratio for 10 to 15 minutes with deionized water. The pH is then about 6. Excess water is drained off leaving a ratio of 5 to 10 parts water to 1 part fiber. During this wash and all following procedures, great care must be taken to avoid contaminating the silica fibers. The use of polyethylene or stainless steel utensils and deionized water aids in avoiding such contamination. The washing procedure has little effect on the bulk chemical composition of the fiber. Its major function is the conditioning and dispersing of the silica fibers.

The alumina fibers are prepared by dispersing them in deionized water. They can be dispersed by mixing 10 to 40 parts water with 1 part fiber in a V-blender for 2½ to 5 minutes. The time required is a function of the fiber length and diameter. In general, the larger the fiber, the more time required.

In order to manufacture ultra low density ceramic material, for example densities below 12 lb/ft$^3$ the process includes the additional steps of:

(1) the addition of expandable carbon fibers in the casting process and/or other temporary support material; and
(2) firing the billet at about 1300° F. to remove the carbon fibers or other support material prior to the final firing at approximately 1600° F. or above.

One preferred composition to practice the invention which can be manufactured using the above method consists of the following:

(1) from about 10% to about 50% by weight alumina fiber;
(2) from about 50% to about 90% by weight silica fiber;
(3) from about 1% to about 3% by weight silicon carbide; and
(4) from about 1% to about 5% by weight boron nitride.

The preferred alumina fibers are 95.2% pure available from ICI Americas, Inc. The preferred silica fibers are 99.7% pure and are available from Manville Corp., Denver, Colo.

One preferred composition is comprised of: a ratio of silica fiber to alumina fiber of 78/22, 2% by weight 600 grit silicon carbide, and 2.85% by weight boron nitride. This composition is available commercially in densities of 3 to 12 (+/−three quarters of a pound) from Lockheed Missiles and Space Co., Inc., Sunnyvale, Calif. ("Lockheed") under the tradename "HTP" (High Temperature Performance). For example, Lockheed commercially sells "HTP-1222" (12 lb/ft.$^3$ density and a silica to alumina fiber ratio of 78/22), "HTP-12-35" (12 lb/ft$^3$ density and a silica/alumina fiber ratio of 65/35) and HTP-12-45 (12 lb./ft$^3$ density and silica/alumina ration of 55/45). In addition, "HTP-6" having various fiber ratios and a 6 lb/ft$^3$ density is also commercially available from Lockheed.

While the above identified fibers are considered the most preferred, it should also be noted that metal silicates, zirconia, and other glass/ceramic fibers can also be used in the composition. Moreover, aluminaborosilicate fibers/glass can be utilized for example, Nextel 312® fibers (a registered trademark of the 3M Co) can also be used in the practice of the present invention. Nextel 312® is a fiber consisting of aluminum oxide, boria and silicon dioxide in the ratio of 3, 1, 2 respectfully. The alumina burosilicate fibers should be prepared in the same manner as the alumina fibers as set forth above.

In addition, while boron nitride is preferred, it is also believed that SiBx, B$_4$C and B and other boron sources can also be used as bonding or fluxing agents. As stated, however, boron nitride is believed to be preferred because it is believed, due to its stability, it permits a more uniform fusion to fiber junction and yields superior bonding and uniform porosity.

It should also be noted, that porous linked fibrous silica fiber (discussed in the previous section) can also be manufactured by the process described above for the manufacture of rigid fused alumina/silica fibers.

According to one embodiment of the invention, 9 lbs/ft$^3$ is the maximum density for mamilian cell growth. According to a further embodiment, for example, a bioreacter, preferred density is dependent upon mean cell diameter, such that maximum cellular integration into the ceramic material occurs between about 100 microns and about 1000 microns. As a further example of a bioreactor embodiment, hepaticytes (liver cells) are grown in about five pounds per cubic foot. For a further bioreactor example, the cell line MG63, about 6.5 pounds per cubic foot are used. As a further sample, about 7.5 pounds per cubic foot is used for fibroblasts. For adipocytes, between about four and about five pounds per cubic foot is used. As yet a further bioreactor example, neuron cells are grown in a density of about 3 pounds per cubic foot.

According to a drug delivery embodiment, in vivo applications, density is such that maximum tissue integration occurs to include blood vessels, nerves, and other normal organ appendages and or cell types. Further, in the in vivo application embodiment, structural archetecture is also provided for (for example, rete peg formation of squamous epithelial tissue). As a further drug delivery embodiment, in dermis for long term drug delivery, between about six and about seven pounds per cubic foot is used. As a further drug delivery embodiment, for short term drug delivery in bone, between about four and about six pounds per cubic foot is used. As yet a further embodiment, the ceramic is shaped as spheres between about 300 microns and about 500 microns in diameter (for example, for BMP release in boney nonunions). As a further drug delivery embodiment, antibiotic release into liver tissue, between about four and about five pounds is used. As still a further example, for antineoplastic delivery to adipose/breast tissue, between about three and about five pounds per cubic foot are used.

Cleaning and Sterilization of Porous Linked Silica Fiber for Cell Culture

Pieces of linked silica fiber blocks about one centimeter square by two to three centimeters long are cut from larger blocks using a diamond blade saw cooled with distilled water. The blocks are washed twice with distilled water and subjected to ultrasonic cleaning for three minutes in absolute ethanol in an ultrasonic bath (Transistor Ultrasonic T14, L&R). The cleaning treatment in ethanol is repeated once. The blocks are dried at 37 degrees Fahrenheit for twenty-four hours and then autoclaved for 20 minutes at 121 degrees Centigrade and 15 psi in glass vials.

Propagation of Cells in Porous Linked Silica Fiber

Approximately 7000 cells are suspended in Dulbecco's Modified Eagle Media (GIBCO Lab, Grand Island, N.Y.) with 10% fetal calf serum. The cells are from a human osteogenic sarcoma MG63 cell line, and are pipetted on to the upper (rough) surface of the linked silica fiber samples positioned in the center of 16 mm wells of 24-well polystyrene culture plates (Corning, Corning, N.Y.). An additional 0.5 ml of media is added to each well. The culture plates are covered and placed in 37 degree Centigrade, humidified incubators in the presence of a 5% $CO_2$ atmosphere.

Colorimetric Assay for Cellular Growth

The method described by Mosmann (J. of Immunological Methods, 65 (1983) 55–63, Rapid Colorimetric Assay for Cellular Growth and Survival: Application to Proliferation and Cytotoxicity Assays, Tim Mosmrann) is used to estimate the growth of cells in the porous linked silica fiber. Briefly, MTT (3-(4,5-dimethylthiazol-2-ol)-2,5-diphenyl tetrazolium bromide (Sigma) is dissolved in phosphate buffered saline (PBS) at 5 mg/ml and filtered to sterilize. 100 ul of MTT solution is added to assay vessels and incubated three hours at 37 degrees Centigrade. The matrix is transferred, or in the instance of wells with no matrix sample, the media and MTT solution is transferred to a centrifuge tube into which 2 milliliters of PBS and 1 ml of 0.04 N Hcl in isopropanol is added. The tubes are vortexed and then incubated at room temperature for 15 minutes. Two hundred and fifty microliters from each well is placed in a microfuge tube and centrifuged in a Microfuge Model 235C (Allied Fischer Scientific) for 2 minutes. Two hundred microliters is transferred to a 96 well microtiter plate. The O.D. at 600 nm is measured in a TiterTek MultiSkan Plus MK2 microtiter reader (Lab Systems 0Y).

Results of Experiment Measuring Cell Growth on Linked Silica Fiber of Low and High Density Using the protocol described above, MG63 cells were incubated on Q-Fiber® linked fiber blocks for six days before harvesting and assessment of cell growth by the calorimetric assay for cell growth detailed above. The blocks with a high density (39 pounds per cubic foot) had low cell growth as indicated by the mean optical density reading of 0.06. The relatively low density blocks of fused fiber ceramic (12 pounds per cubic foot) supported increased growth of cells that resulted in production of a mean optical density reading of 0.16. There is a linear relationship between optical density reading and number of MG63 cells such that a colored product from MMT metabolism results in optical density of 1.0 O.D. at 260 nm for 470,000 cells.

From these results one can conclude that for a given fibrous material, in vitro cell growth rate is substantially inversely related to density of the material. Note that the cells placed on the high density material fail to penetrate the material as deeply as cells placed on the low density material.

Results of Experiment Measuring Cell Growth on Linked Silica Fiber of Different Dimensions The protocol described above was used except that 10,000 MG63 cells were incubated per well. Q-Fiber® ceramic blocks of 12 pounds per cubic foot of 3 mm, 6 mm and 8 mm thicknesses and 1 square centimeter were incubated for three days. The optical density reading for the 3 mm block was 0.19, for the 6 mm block was 0.22 and for the 8 mm was 0.374.

From these results one can conclude that the larger the area of the block, the greater is the cell growth rate. One would anticipate that increasing the size of the block will increase the capability to Support growth of larger numbers of cells up to the limit of the media or tissue fluid to supply nutrients within the center of the matrix.

The use of flowing media or tissue fluid moving continuously through porous linked fibrous biomaterial to replenish nutrients and remove metabolic products in large blocks of matrices filled with cells is the essence of a continuous bioreactor. Preferred embodiments of reservoirs of the present invention which contain cultured cells function in this manner.

What is claimed is:

1. An implantable drug delivery system comprising:
    a porous linked fibrous substantially non-biodegradable biomaterial, the biomaterial having a plurality of voids of at least one predetermined size range; and
    at least one drug dispersed within the voids of the biomaterial;
    wherein at least a selected portion of the voids have a predetermined size range effective to stimulate angiogenesis when the system is implanted in bone or vascular tissue, and the biomaterial consists of nonwoven, randomly-oriented fibers linked together at a variety of cross-points.

2. The system on claim 1, further comprising the biomaterial having a plurality of voids of at least two predetermined size ranges, wherein at least a first selected portion of the voids have a predetermined size range effective to stimulate angiogenesis when the system is implanted in bone or vascular tissue, and wherein at least a second portion of the voids have a predetermined size range effective to release the drug at a calculated rate when the system in implanted in bone or vascular tissue.

3. The system of claim 1, wherein the predetermined size range of the plurality of voids is between approximately 100 and 1000 microns in diameter.

4. The system of claim 1, further comprising the biomaterial having a plurality of voids of at least one predetermined mean void space.

5. The system of claim 1, further comprising the drug dispersed within a biodegradable matrix.

6. The system of claim 5, wherein the biodegradable matrix comprises a material selected from the group consisting of: polyparadioxanon, polylysine, polyglycolic acid, polylactic acid, homopolymers thereof, copolymers thereof, and combinations thereof.

7. The system of claim 5, wherein the bioegradable matrix is augmented with a material selected from the group consisting of: GLASSFIBER plaster of Paris, beta-whitlockite, hydroxyapatite, calcium phosphate ceramics, and combinations thereof.

8. The system of claim 5, wherein the biodegradable matrix is operable to control release of the drug when the system is implanted in bone or vascular tissue.

9. The system of claim 1, wherein the drug comprises an antibiotic.

10. The system of claim 1, wherein the drug comprises a synthetic or natural hormone.

11. The system of claim 1, wherein the system is implanted in the vasculature of an animal.

12. The system of claim 1, wherein the system is implanted in the bone of an animal.

* * * * *

UNITED STATES PATENT AND TRADEMARK OFFICE
CERTIFICATE OF CORRECTION

PATENT NO. : 7,037,304 B2  Page 1 of 1
APPLICATION NO. : 09/961479
DATED : May 2, 2006
INVENTOR(S) : Lyles et al.

It is certified that error appears in the above-identified patent and that said Letters Patent is hereby corrected as shown below:

Title page, Item [63]. Please delete the entire paragraph and replace with
-- Continuation of application No. 09/170,574 filed on Oct. 13, 1998, now Pat. No. 6,340,360, which is a continuation of application No. 08/569,107, filed on Mar. 18, 1996, now Pat. No. 5,964,745, which is a 371 application of PCT/US94/07581, filed on July 1, 1994, which is a continuation-in-part of application No. 08/087,615, filed on Jul. 2, 1993, now abandoned.--

Column 1, Line 5, after "Mar. 18, 2006," delete "which is a 371 of PCT/US94/07581, now U.S. Pat. No. 5,964,745" and insert -- now Pat. No. 5,964,745, which is a 371 application of PCT/US94/07581, filed on July 1, 1994 --.

Signed and Sealed this

Twenty-seventh Day of November, 2007

JON W. DUDAS
*Director of the United States Patent and Trademark Office*